(12) United States Patent
Griffin

(10) Patent No.: US 10,130,372 B2
(45) Date of Patent: Nov. 20, 2018

(54) OCCLUSION DEVICE

(71) Applicant: Cerus Endovascular Limited, Oxford (GB)

(72) Inventor: Stephen Griffin, San Jose, CA (US)

(73) Assignee: Cerus Endovascular Limited, Oxford (GB)

( * ) Notice: Subject to any disclaimer, the term of this patent is extended or adjusted under 35 U.S.C. 154(b) by 0 days.

(21) Appl. No.: 14/699,188

(22) Filed: Apr. 29, 2015

(65) Prior Publication Data

US 2015/0313605 A1 Nov. 5, 2015

Related U.S. Application Data

(60) Provisional application No. 62/083,672, filed on Nov. 24, 2014, provisional application No. 61/986,369, filed on Apr. 30, 2014.

(51) Int. Cl.
*A61M 29/00* (2006.01)
*A61B 17/12* (2006.01)
(Continued)

(52) U.S. Cl.
CPC ........ *A61B 17/12172* (2013.01); *A61B 17/12* (2013.01); *A61B 17/12031* (2013.01);
(Continued)

(58) Field of Classification Search
CPC ........ A61B 17/12172; A61B 17/12022; A61B 17/12113; A61B 2017/00867;
(Continued)

(56) References Cited

U.S. PATENT DOCUMENTS 2,849,002 A 8/1958 Oddo
3,480,017 A 11/1969 Shute
(Continued)

FOREIGN PATENT DOCUMENTS

DE 102008015781 9/2011
DE 102011102955 12/2012
(Continued)

OTHER PUBLICATIONS

Altes et al., Creation of Saccular Aneurysms in the Rabbit: A Model Suitable for Testing Endovascular Devices. AJR 2000; 174: 349-354.
(Continued)

*Primary Examiner* — Katherine M Shi
(74) *Attorney, Agent, or Firm* — Fish & Richardson P.C.

(57) ABSTRACT

Provided herein is an occlusion device for intrasaccular implantation and/or vascular occlusion comprising: (a) a substantially solid marker having a proximal end, and a distal end; and (b) a low profile resilient mesh body attached to the distal end of the marker, the body having a delivery shape and a deployed shape capable of conforming to aneurysm walls; wherein the body has a diameter greater than a diameter of an aneurysm to be treated. Also provided herein is a kit comprising the occlusion device disclosed herein and a means for delivery thereof. Methods of manufacture and use of the occlusion device disclosed herein are also disclosed.

15 Claims, 5 Drawing Sheets

(51) Int. Cl.
*A61B 90/00* (2016.01)
*A61B 17/00* (2006.01)

(52) U.S. Cl.
CPC .. *A61B 17/12113* (2013.01); *A61B 17/12168* (2013.01); *A61B 90/39* (2016.02); *A61B 2017/00867* (2013.01); *A61B 2017/1205* (2013.01); *A61B 2017/12063* (2013.01); *A61B 2090/3937* (2016.02)

(58) Field of Classification Search
CPC ........ A61B 2017/1205; A61B 17/0057; A61B 2017/12063; A61B 90/39; A61B 17/12031; A61B 17/12036; A61B 17/1204; A61B 17/12118
USPC .................................................. 606/194, 200
See application file for complete search history.

(56) References Cited

U.S. PATENT DOCUMENTS

| | | |
|---|---|---|
| 4,364,392 A | 12/1982 | Strother et al. |
| 4,395,806 A | 8/1983 | Wonder et al. |
| 4,545,367 A | 10/1985 | Tucci |
| 4,836,204 A | 6/1989 | Landymore et al. |
| 4,991,602 A | 2/1991 | Amplatz et al. |
| 5,002,556 A | 3/1991 | Ishida et al. |
| 5,025,060 A | 6/1991 | Yabuta et al. |
| 5,065,772 A | 11/1991 | Cox, Jr. |
| 5,067,489 A | 11/1991 | Lind |
| 5,122,136 A | 6/1992 | Guglielmi et al. |
| 5,192,301 A | 3/1993 | Kamiya et al. |
| 5,423,829 A | 6/1995 | Pham et al. |
| 5,624,449 A | 4/1997 | Pham et al. |
| 5,733,294 A | 3/1998 | Forber et al. |
| 5,891,128 A | 4/1999 | Gia et al. |
| 5,928,260 A | 7/1999 | Chin et al. |
| 6,007,573 A | 12/1999 | Wallace et al. |
| 6,024,756 A | 2/2000 | Pham |
| 6,080,191 A | 6/2000 | Thaler |
| 6,096,021 A | 8/2000 | Helm et al. |
| 6,113,609 A | 9/2000 | Adams |
| 6,123,714 A | 9/2000 | Gia et al. |
| 6,168,622 B1 | 1/2001 | Mazzocchi |
| 6,221,086 B1 | 4/2001 | Forber |
| 6,270,515 B1 | 8/2001 | Linden et al. |
| 6,315,787 B1 | 11/2001 | Tsugita et al. |
| 6,334,048 B1 | 12/2001 | Edvardsson et al. |
| 6,419,686 B1 | 7/2002 | McLeod et al. |
| 6,454,780 B1 | 9/2002 | Wallace |
| 6,463,317 B1 | 10/2002 | Kucharczyk et al. |
| 6,506,204 B2 | 1/2003 | Mazzocchi |
| 6,527,919 B1 | 3/2003 | Roth |
| 6,547,804 B2 | 4/2003 | Porter et al. |
| 6,551,303 B1 | 4/2003 | Van Tassel et al. |
| 6,569,190 B2 | 5/2003 | Whalen, II et al. |
| 6,589,230 B2 | 7/2003 | Gia et al. |
| 6,589,256 B2 | 7/2003 | Forber |
| 6,605,102 B1 | 8/2003 | Mazzocchi et al. |
| 6,620,152 B2 | 9/2003 | Guglielmi |
| 6,669,719 B2 | 12/2003 | Wallace et al. |
| 6,689,159 B2 | 2/2004 | Lau et al. |
| 6,780,196 B2 | 8/2004 | Chin et al. |
| 6,833,003 B2 | 12/2004 | Jones et al. |
| 6,855,154 B2 | 2/2005 | Abdel-Gawwad |
| 6,949,116 B2 | 9/2005 | Solymar et al. |
| 7,044,134 B2 | 5/2006 | Khairkhahan et al. |
| 7,093,527 B2 | 8/2006 | Rapaport et al. |
| 7,128,736 B1 | 10/2006 | Abrams et al. |
| 7,152,605 B2 | 12/2006 | Khairkhahan et al. |
| 7,195,636 B2 | 3/2007 | Avellanet et al. |
| 7,229,454 B2 | 6/2007 | Tran et al. |
| 7,229,461 B2 | 6/2007 | Chin et al. |
| 7,371,249 B2 | 5/2008 | Douk et al. |
| 7,410,482 B2 | 8/2008 | Murphy et al. |
| 7,597,704 B2 | 10/2009 | Frazier et al. |
| 7,695,488 B2 | 4/2010 | Berenstein et al. |
| 7,744,652 B2 | 6/2010 | Morsi |
| 8,034,061 B2 | 10/2011 | Amplatz et al. |
| 8,075,585 B2 | 12/2011 | Lee et al. |
| 8,142,456 B2 | 3/2012 | Rosqueta et al. |
| 8,221,483 B2 | 7/2012 | Ford et al. |
| 8,261,648 B1 | 9/2012 | Marchand et al. |
| 8,361,106 B2 | 1/2013 | Solar et al. |
| 8,361,138 B2 | 1/2013 | Adams |
| 8,372,114 B2 | 2/2013 | Hines |
| 8,398,671 B2 | 3/2013 | Chen |
| 8,430,012 B1 | 4/2013 | Marchand et al. |
| 8,454,633 B2 | 6/2013 | Amplatz et al. |
| 8,523,897 B2 | 9/2013 | van der Burg et al. |
| 2002/0082638 A1 | 6/2002 | Porter et al. |
| 2002/0143349 A1 | 10/2002 | Gifford, III et al. |
| 2002/0188314 A1 | 12/2002 | Anderson et al. |
| 2003/0120337 A1 | 6/2003 | Van Tassel et al. |
| 2003/0176884 A1* | 9/2003 | Berrada .............. A61F 2/013 606/200 |
| 2003/0181927 A1 | 9/2003 | Wallace |
| 2003/0195553 A1 | 10/2003 | Wallace et al. |
| 2004/0034366 A1 | 2/2004 | van der Burg et al. |
| 2004/0044391 A1* | 3/2004 | Porter .............. A61B 17/12022 623/1.1 |
| 2004/0087998 A1 | 5/2004 | Lee et al. |
| 2004/0098027 A1 | 5/2004 | Teoh et al. |
| 2004/0127935 A1 | 7/2004 | Van Tassel et al. |
| 2004/0133222 A1 | 7/2004 | Tran et al. |
| 2004/0254594 A1 | 12/2004 | Alfaro |
| 2005/0021016 A1 | 1/2005 | Malecki et al. |
| 2005/0251200 A1 | 11/2005 | Porter |
| 2006/0052816 A1 | 3/2006 | Bates et al. |
| 2006/0058735 A1 | 3/2006 | Lesh |
| 2006/0064151 A1* | 3/2006 | Guterman ........ A61B 17/12022 623/1.3 |
| 2006/0155323 A1 | 7/2006 | Porter et al. |
| 2006/0155367 A1 | 7/2006 | Hines |
| 2006/0167494 A1 | 7/2006 | Suddaby |
| 2007/0106311 A1 | 5/2007 | Wallace et al. |
| 2007/0173928 A1 | 7/2007 | Morsi |
| 2007/0208376 A1* | 9/2007 | Meng ................. A61B 17/0057 606/213 |
| 2007/0288083 A1 | 12/2007 | Hines |
| 2008/0097495 A1 | 4/2008 | Feller, III et al. |
| 2009/0281557 A1 | 11/2009 | Sander et al. |
| 2010/0069948 A1 | 3/2010 | Veznedaroglu et al. |
| 2011/0046658 A1 | 2/2011 | Connor et al. |
| 2011/0319978 A1 | 12/2011 | Schaffer |
| 2012/0283768 A1 | 11/2012 | Cox et al. |
| 2012/0330341 A1 | 12/2012 | Becking et al. |
| 2013/0035712 A1 | 2/2013 | Theobald et al. |
| 2013/0066357 A1 | 3/2013 | Aboytes et al. |
| 2013/0190800 A1* | 7/2013 | Murphy .......... A61B 17/12022 606/198 |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0257360 A1* | 9/2014 | Keillor ............... A61B 17/0057 606/198 |
| 2014/0343602 A1* | 11/2014 | Cox .................. A61B 17/0057 606/215 |

FOREIGN PATENT DOCUMENTS

| | | |
|---|---|---|
| DE | 102009058132 | 7/2014 |
| DE | 202008018523 | 4/2015 |
| DE | 102013106031 | 7/2015 |
| DE | 102012107175 | 8/2015 |
| EP | 0836450 B1 | 4/1988 |
| EP | 0902704 B1 | 3/1999 |
| EP | 1003422 A1 | 5/2000 |
| EP | 1054635 B1 | 11/2000 |
| EP | 1295563 B1 | 3/2003 |
| EP | 1295563 B1 | 3/2003 |
| EP | 1441649 B1 | 8/2004 |
| EP | 1483009 B1 | 12/2004 |

(56) References Cited

FOREIGN PATENT DOCUMENTS

| | | |
|---|---|---|
| EP | 1494619 B1 | 1/2005 |
| EP | 1651117 B1 | 3/2005 |
| EP | 1527753 B1 | 5/2005 |
| EP | 1569565 B1 | 9/2005 |
| EP | 1574169 B1 | 9/2005 |
| EP | 1633275 A2 | 3/2006 |
| EP | 1659988 B1 | 5/2006 |
| EP | 1725185 B1 | 11/2006 |
| EP | 1804719 A2 | 7/2007 |
| EP | 1862122 A1 | 12/2007 |
| EP | 1923005 B1 | 5/2008 |
| EP | 2063791 | 6/2009 |
| EP | 2134263 B1 | 12/2009 |
| EP | 2157937 B1 | 3/2010 |
| EP | 2207500 A1 | 7/2010 |
| EP | 2244666 A1 | 11/2010 |
| EP | 2265193 B1 | 12/2010 |
| EP | 2266465 B1 | 12/2010 |
| EP | 2279023 A2 | 2/2011 |
| EP | 2324775 B1 | 5/2011 |
| EP | 2349024 A2 | 8/2011 |
| EP | 2367482 B1 | 9/2011 |
| EP | 2387951 B1 | 11/2011 |
| EP | 2460476 A3 | 6/2012 |
| EP | 2468349 A1 | 6/2012 |
| EP | 2496299 A2 | 9/2012 |
| EP | 2506808 B1 | 10/2012 |
| EP | 2543345 A1 | 1/2013 |
| EP | 2567663 A1 | 3/2013 |
| EP | 2613709 A1 | 7/2013 |
| EP | 2617386 A1 | 7/2013 |
| EP | 2647343 A3 | 10/2013 |
| EP | 2677944 A1 | 1/2014 |
| EP | 2744412 A1 | 6/2014 |
| EP | 2848211 A1 | 3/2015 |
| EP | 2854704 B1 | 4/2015 |
| EP | 2887887 A1 | 7/2015 |
| EP | 2923674 B1 | 9/2015 |
| EP | 2926744 A1 | 10/2015 |
| EP | 2943152 A1 | 11/2015 |
| EP | 2964105 A1 | 1/2016 |
| EP | 3068337 A1 | 9/2016 |
| EP | 3131515 A1 | 2/2017 |
| EP | 3136986 A1 | 3/2017 |
| EP | 3148481 A1 | 4/2017 |
| JP | 2013537069 A | 9/2013 |
| WO | WO2006034149 A2 | 3/2006 |
| WO | WO2009132045 A2 | 10/2009 |
| WO | WO2012099704 A2 | 7/2012 |
| WO | WO2012099909 A2 | 7/2012 |
| WO | WO2013016618 A2 | 1/2013 |
| WO | WO2013109309 A1 | 7/2013 |
| WO | 15187196 A1 | 12/2015 |
| WO | 16107357 A1 | 7/2016 |
| WO | 16137997 A1 | 9/2016 |

OTHER PUBLICATIONS

Schaffer, Advanced Materials & Processes, Oct 2002, pp. 51-54.
International Search Report which dated Jul. 6, 2015 in corresponding application No. PCT/EP2015/059429.

* cited by examiner

OCCLUSION DEVICE

RELATED APPLICATIONS

This application claims priority to U.S. Provisional Application No. 61/986,369, filed Apr. 30, 2014, and U.S. Provisional Application No. 61/083,672, filed Nov. 24, 2014, the disclosures of which are hereby incorporated herein by reference in their entirety. In addition, all documents and references cited herein and in the above referenced applications, are hereby incorporated herein by reference.

FIELD OF THE INVENTION

The present invention relates generally to the field of occlusion devices and/or occlusion device systems and/or implantable occlusion devices and the use of the same for the treatment and/or amelioration of aneurysms.

BACKGROUND OF THE DISCLOSURE

There is a significant demand for the development of improved occlusion-type devices and/or systems for the treatment and/or amelioration of aneurysms. This observation is supported by the abundance and wide-range of current occlusion devices and/or systems currently in the aneurysm treatment field. However, there still remains an unmet need for providing aneurysm treatment and/or amelioration, particularly for neurovascular aneurysms, via occlusion devices comprised of a minimum amount of fully-retrievable deployable material.

It is well known that an aneurysm forms when a dilated portion of an artery is stretched thin from the pressure of the blood. The weakened part of the artery forms a bulge, or a ballooning area, that risks leak and/or rupture. When a neurovascular aneurysm ruptures, it causes bleeding into the compartment surrounding the brain, the subarachnoid space, causing a subarachnoid hemorrhage. Subarachnoid hemorrhage from a ruptured neurovascular aneurysm can lead to a hemorrhagic stroke, brain damage, and death. Approximately 25 percent of all patients with a neurovascular aneurysm suffer a subarachnoid hemorrhage. Neurovascular aneurysms occur in two to five percent of the population and more commonly in women than men. It is estimated that as many as 18 million people currently living in the United States will develop a neurovascular aneurysm during their lifetime. Annually, the incidence of subarachnoid hemorrhage in the United States exceeds 30,000 people. Ten to fifteen percent of these patients die before reaching the hospital and over 50 percent die within the first thirty days after rupture. Of those who survive, about half suffer some permanent neurological deficit.

Smoking, hypertension, traumatic head injury, alcohol abuse, use of hormonal contraception, family history of brain aneurysms, and other inherited disorders such as Ehlers-Danlos syndrome (EDS), polycystic kidney disease, and Marfan syndrome possibly contribute to neurovascular aneurysms.

Most unruptured aneurysms are asymptomatic. Some people with unruptured aneurysms experience some or all of the following symptoms: peripheral vision deficits, thinking or processing problems, speech complications, perceptual problems, sudden changes in behavior, loss of balance and coordination, decreased concentration, short term memory difficulty, and fatigue. Symptoms of a ruptured neurovascular aneurysm include nausea and vomiting, stiff neck or neck pain, blurred or double vision, pain above and behind the eye, dilated pupils, sensitivity to light, and loss of sensation. Sometimes patients describing "the worst headache of my life" are experiencing one of the symptoms of a ruptured neurovascular aneurysm.

Most aneurysms remain undetected until a rupture occurs. Aneurysms, however, may be discovered during routine medical exams or diagnostic procedures for other health problems. Diagnosis of a ruptured cerebral aneurysm is commonly made by finding signs of subarachnoid hemorrhage on a CT scan (Computerized Tomography). If the CT scan is negative but a ruptured aneurysm is still suspected, a lumbar puncture is performed to detect blood in the cerebrospinal fluid (CSF) that surrounds the brain and spinal cord.

To determine the exact location, size, and shape of an aneurysm, neuroradiologists use either cerebral angiography or tomographic angiography. Cerebral angiography, the traditional method, involves introducing a catheter into an artery (usually in the leg) and steering it through the blood vessels of the body to the artery involved by the aneurysm. A special dye, called a contrast agent, is injected into the patient's artery and its distribution is shown on X-ray projections. This method may not detect some aneurysms due to overlapping structures or spasm.

Computed Tomographic Angiography (CTA) is an alternative to the traditional method and can be performed without the need for arterial catheterization. This test combines a regular CT scan with a contrast dye injected into a vein. Once the dye is injected into a vein, it travels to the brain arteries, and images are created using a CT scan. These images show exactly how blood flows into the brain arteries. New diagnostic modalities promise to supplement both classical and conventional diagnostic studies with less-invasive imaging and possibly provide more accurate 3-dimensional anatomic information relative to aneurismal pathology. Better imaging, combined with the development of improved minimally invasive treatments, will enable physicians to increasingly detect, and treat, more silent aneurysms before problems arise.

Several methods of treating aneurysms have been attempted, with varying degrees of success. For example, open craniotomy is a procedure by which an aneurysm is located, and treated, extravascularly. This type of procedure has significant disadvantages. For example, the patient undergoes a great deal of trauma in the area of the aneurysm by virtue of the fact that the surgeon must sever various tissues in order to reach the aneurysm. In treating cerebral aneurysms extravascularly, for instance, the surgeon must typically remove a portion of the patient's skull, and must also traumatize brain tissue in order to reach the aneurysm. As such, there is a potential for the development of epilepsy in the patients due to the surgery.

Other techniques used in treating aneurysms are performed endovascularly. Such techniques typically involve attempting to form a mass within the sac of the aneurysm. Typically, a microcatheter is used to access the aneurysm. The distal tip of the microcatheter is placed within the sac of the aneurysm, and the microcatheter is used to inject embolic material into the sac of the aneurysm. The embolic material includes, for example, detachable coils or an embolic agent, such as a liquid polymer. The injection of these types of embolic materials suffers from disadvantages, most of which are associated with migration of the embolic material out of the aneurysm into the parent artery. This can cause permanent and irreversible occlusion of the parent artery.

For example, when detachable coils are used to occlude an aneurysm which does not have a well-defined neck region, the detachable coils can migrate out of the sac of the aneurysm and into the parent artery. Further, it is at times difficult to gauge exactly how full the sac of the aneurysm is when detachable coils are deployed. Therefore, there is a risk of overfilling the aneurysm in which case the detachable coils also spill out into the parent artery.

Another disadvantage of detachable coils involves coil compaction over time. After filling the aneurysm, there remains space between the coils. Continued hemodynamic forces from the circulation act to compact the coil mass resulting in a cavity in the aneurysm neck. Thus, the aneurysm can recanalize.

Embolic agent migration is also a problem. For instance, where a liquid polymer is injected into the sac of the aneurysm, it can migrate out of the sac of the aneurysm due to the hemodynamics of the system. This can also lead to irreversible occlusion of the parent vessel.

Techniques have been attempted in order to deal with the disadvantages associated with embolic material migration to the parent vessel. Such techniques are, without limitation, temporary flow arrest and parent vessel occlusion, and typically involve temporarily occluding the parent vessel proximal of the aneurysm, so that no blood flow occurs through the parent vessel, until a thrombotic mass has formed in the sac of the aneurysm. In theory, this helps reduce the tendency of the embolic material to migrate out of the aneurysm sac. However, it has been found that a thrombotic mass can dissolve through normal lysis of blood. Also, in certain cases, it is highly undesirable from a patient's risk/benefit perspective to occlude the parent vessel, even temporarily. Therefore, this technique is, at times, not available as a treatment option. In addition, it is now known that even occluding the parent vessel may not prevent all embolic material migration into the parent vessel.

Another endovascular technique for treating aneurysms involves inserting a detachable balloon into the sac of the aneurysm using a microcatheter. The detachable balloon is then inflated using saline and/or contrast fluid. The balloon is then detached from the microcatheter and left within the sac of the aneurysm in an attempt to fill the sac of the aneurysm. However, detachable balloons also suffer disadvantages and as such this practice has all but been superseded by the current practice of deployment of coils or other types of occlusion devices. For example, detachable balloons, when inflated, typically will not conform to the interior configuration of the aneurysm sac. Instead, the detachable balloon requires the aneurysm sac to conform to the exterior surface of the detachable balloon. Thus, there is an increased risk that the detachable balloon will rupture the sac of the aneurysm. Further, detachable balloons can rupture and migrate out of the aneurysm.

Another endovascular technique for treating aneurysms involves occlusion devices having two expandable lobes and a waist, or an expandable body portion, a neck portion, and a base portion.

Still another endovascular technique for treating aneurysms involves occlusion devices for intrasaccular implantation having a body portion designed to fill and/or expand radially into the space within the sac of the aneurysm.

While such occlusion devices may be found, for example in U.S. Pat. Nos. 5,025,060; 5,928,260; 6,168,622; 6,221,086; 6,334,048; 6,419,686; 6,506,204; 6,605,102; 6,589,256; 6,780,196; 7,044,134; 7,093,527; 7,128,736; 7,152,605; 7,229,461; 7,410,482; 7,597,704; 7,695,488; 8,034,061; 8,142,456; 8,261,648; 8,361,138; 8,430,012; 8,454,633; and 8,523,897; and United States Application Numbers 2003/0195553; 2004/0098027; 2006/0167494; 2007/0288083; 2010/0069948; 2011/0046658; 2012/0283768; 2012/0330341; and 2013/0035712; European Application Number EP 1651117; and International Application Number WO13/109309; none of these references disclose the embodiments of the occlusion device disclosed herein.

Therefore, the present invention provides innovative improvements and several advantages in the field of vascular occlusion devices because the occlusion device disclosed herein provides aneurysm treatment and/or amelioration, particularly for neurovascular aneurysms, via the use of a minimum amount of fully-retrievable deployable material. The configuration of such an oversized occlusion device eliminates the need for additional material for pinning the aneurysm neck and/or for an anchoring mechanism in the parent vessel adjacent to the aneurysm and/or for spherical, radial expansion of the body portion of the device into the sac of the aneurysm.

All documents and references cited herein and in the referenced patent documents, are hereby incorporated herein by reference.

SUMMARY OF THE INVENTION

The present inventor has designed an occlusion device for providing aneurysm treatment and/or amelioration through the use of a minimum amount of fully-retrievable deployable low profile resilient mesh material which is oversized to the diameter of the aneurysm. As such, an occlusion device, having less material than the current standard device, minimizes the need for anti-coagulation therapy and/or lessens the risk of clot emboli formation which could flow deeper into the vascular tree inducing stroke. Such an implantable occlusion device is also used for treatment of vessel occlusion and/or peripheral vascular embolization.

Disclosed herein is an occlusion device for intrasaccular implantation comprising: (a) a substantially solid marker having a proximal end, and a distal end; and (b) a low profile resilient mesh body attached to the distal end of the marker, the body having a delivery shape and a deployed shape capable of conforming to aneurysm walls; wherein the body has a diameter greater than a diameter of an aneurysm to be treated.

In another embodiment, the resilient mesh body of the occlusion device is single-layer mesh.

In another embodiment, the resilient mesh body of the occlusion device is a dual or double layer mesh. In a further embodiment, the dual layer of mesh comprises a single layer of mesh folded circumferentially.

In another embodiment, the deployed shape of the resilient mesh body of the occlusion device is capable of apposing an aneurysm dome.

In another embodiment, the proximal end of the marker of the occlusion device is capable of sealing an aneurysm neck. In further embodiments, the marker is a radiopaque marker, the marker is a detachment junction to deploy the occlusion device, the marker is an attachment junction to retrieve the occlusion device, the marker comprises a rigid member, and/or the marker is a solid ring.

Also disclosed herein is a kit comprising the occlusion device disclosed herein and a delivery means for deploying the occlusion device.

Also disclosed herein is an implantable device for vessel occlusion comprising: (a) a substantially solid marker having a proximal end, and a distal end; and (b) a low profile resilient mesh body attached to the distal end of the marker, the body having a delivery shape and a deployed shape capable of conforming to vessel walls; wherein the body has a diameter greater than a diameter of a vessel to be treated.

In another embodiment, the body of the occlusion device is a single layer of mesh.

In another embodiment, the body of the occlusion device is a dual or double layer of mesh. In a further embodiment, the dual layer of mesh comprises a single layer of mesh folded circumferentially.

Additionally disclosed herein is an implantable device for vessel occlusion comprising: (a) a substantially solid marker having a proximal end, and a distal end; and (b) a resilient mesh body attached to the distal end of the marker, the body having a delivery shape and a deployed shape capable of conforming to vessel walls; wherein the body is a dual layer of mesh comprising a circumferential fold line. In another embodiment, the resilient mesh body of the occlusion device is a low profile resilient mesh body.

Additionally disclosed herein is an occlusion device comprising: (a) a substantially solid marker having a proximal end, and a distal end; and (b) a resilient mesh body attached to the distal end of the marker, the body having a delivery shape and a deployed shape capable of conforming to vessel or aneurysm walls; wherein the body has a diameter greater than a diameter of an aneurysm or vessel to be treated; and wherein the body has a height that is between about 10-20% of its width.

Additionally disclosed herein are methods for manufacture and/or delivery and/or deployment of the occlusion device disclosed herein.

In other embodiments, the occlusion device in the preceding paragraphs may incorporate any of the preceding or subsequently disclosed embodiments.

The Summary of the Invention is not intended to define the claims nor is it intended to limit the scope of the invention in any manner.

Other features and advantages of the invention will be apparent from the following Drawings, Detailed Description, and the Claims.

BRIEF DESCRIPTION OF THE FIGURES

FIG. 1A shows the diameter (x) of the occlusion device in free air. FIG. 1B shows a cross-sectional view of the occlusion device deployed in an aneurysm having a diameter (y).

FIG. 2A shows the device in its delivery shape. FIG. 2B shows the device deploying in a manner in which the compacted ends of the mesh material open in an outward manner. FIG. 2C shows the device in its deployed shape.

FIG. 3A shows the diameter (x) of the occlusion device having a circumferential fold line and a dual or double layer of mesh material. FIG. 3B shows a dual layer occlusion device disclosed herein deployed in an aneurysm having a diameter (y).

FIG. 4A shows a dual layer occlusion device in its delivery shape. FIG. 4B shows the dual layer occlusion device deploying in a manner in which the compacted ends of the device open in an outward manner. FIG. 4C shows the flattening effect/increase in width/increase in diameter of the dual/double layer of mesh material of the device in its deployed state.

FIG. 5A shows the delivery of a dual layer occlusion device via a catheter and/or guide wire having electrolytic means. FIG. 5B shows electrolytic detachment of the core wire or guide wire from the occlusion device.

DETAILED DESCRIPTION

Figure 1A:
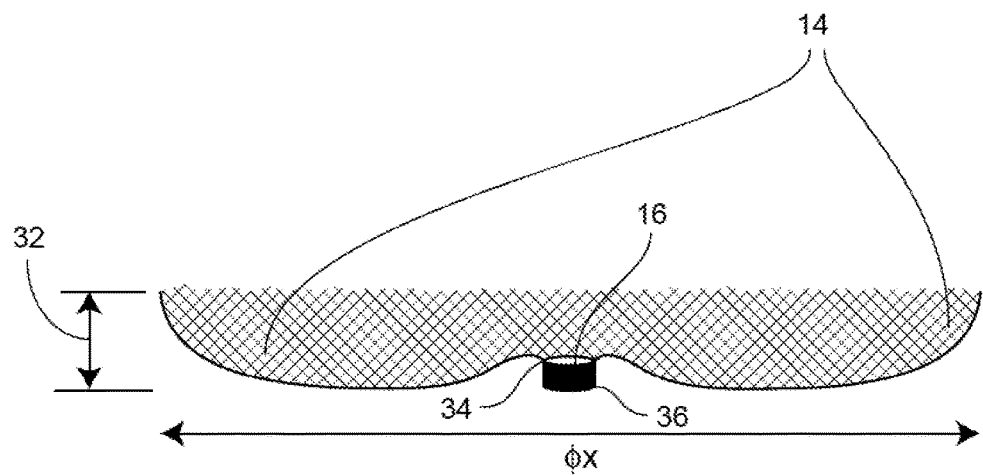
FIG. 1A-1B illustrates perspective views of an embodiment of an occlusion device disclosed herein.

The present invention is illustrated in the drawings and description in which like elements are assigned the same reference numerals. However, while particular embodiments are illustrated in the drawings, there is no intention to limit the present invention to the specific embodiment or embodiments disclosed. Rather, the present invention is intended to cover all modifications, alternative constructions, and equivalents falling within the spirit and scope of the invention. As such, the drawings are intended to be illustrative and not restrictive.

Unless otherwise defined, all technical terms used herein have the same meaning as commonly understood by one of ordinary skill in the art to which this technology belongs.

Exemplary embodiments of the present invention are depicted in FIGS. 1-5.

For the purposes of the present invention, the terminology "corresponds to" means there is a functional and/or mechanical relationship between objects which correspond to each other. For example, an occlusion device delivery system corresponds to (or is compatible with) an occlusion device for deployment thereof.

For the purposes of the present invention, the terminology "occlusion device" means and/or may be interchangeable with terminology such as, without limitation, "device" or "occlusion device system" or "occlusion system" or "system" or "occlusion device implant" or "implant" or "intrasaccular implant" and the like.

Occlusion device delivery systems are well known and readily available in the art. For example, such delivery technologies may be found, without limitation, in U.S. Pat. Nos. 4,991,602; 5,067,489; 6,833,003; 2006/0167494; and 2007/0288083; each of the teachings of which are incorporated herein. For the purposes of the present invention, any type of occlusion device delivery means and/or delivery system and/or delivery technology and/or delivery mechanism and/or detachment (and/or attachment) means and/or detachment system and/or detachment technology and/or detachment mechanism may be utilized and/or modified in such a manner as to make compatible (so as to correspond) with the occlusion device disclosed herein. Exemplary occlusion device delivery mechanisms and/or systems include, without limitation, guide wires, pusher wires, catheters, micro-catheters, and the like. Exemplary occlusion device detachment mechanisms include, without limitation, fluid pressure, electrolytic mechanisms, hydraulic mechanisms, interlocking mechanisms, and the like. In one embodiment, the occlusion device disclosed herein is used in a method of electrolytic detachment. Electrolytic detachment is well known in the art and can be found, for example, in U.S. Pat. Nos. 5,122,136; 5,423,829; 5,624,449; 5,891, 128; 6,123,714; 6,589,230; and 6,620,152.

Figure 3A:
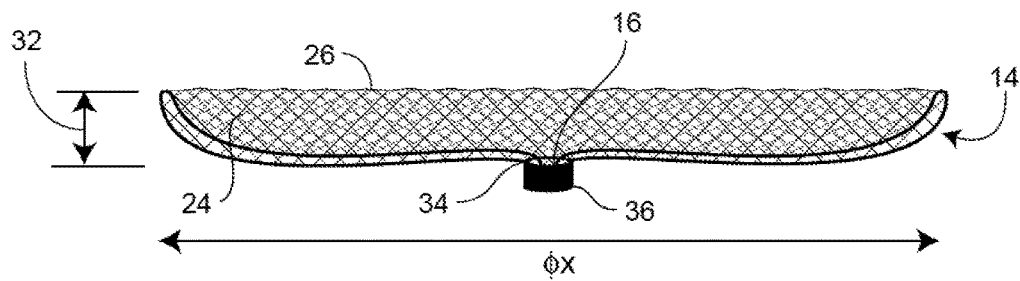
FIG. 3A-3B illustrates perspective views of an embodiment of the occlusion device disclosed herein.

FIG. 1A and FIG. 3A show an embodiment of an occlusion device as disclosed herein for intrasaccular implantation within an 10 aneurysm to be treated. FIG. 1A and FIG.

Figure 1B:
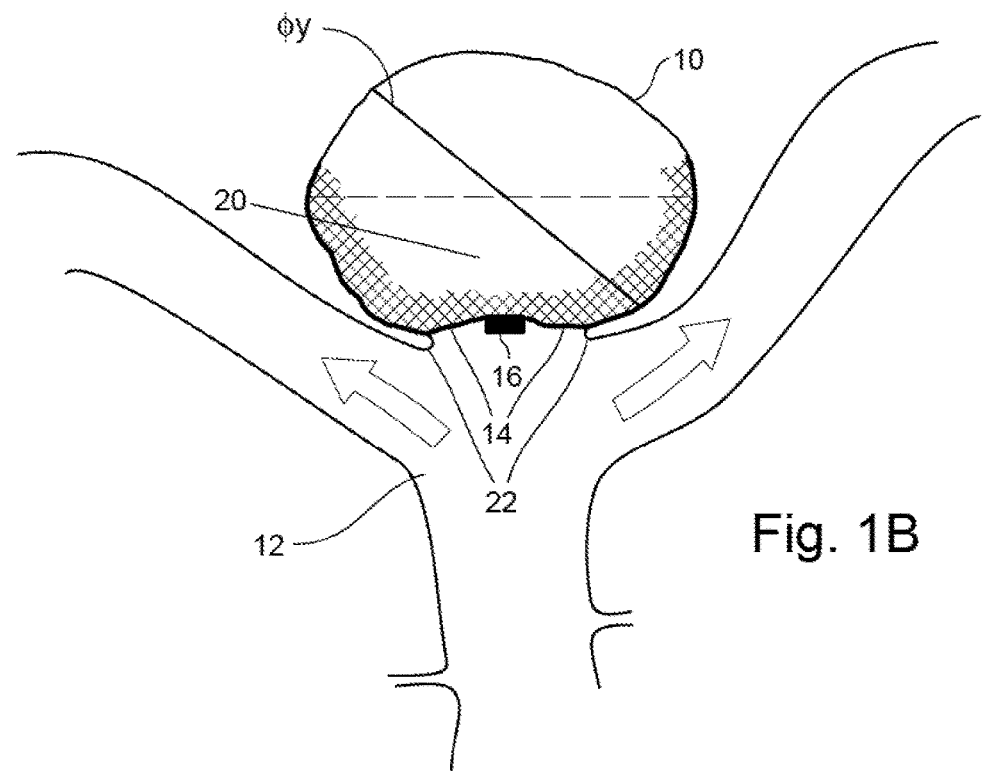

3A also shows the diameter (x) of the 14 resilient mesh body of such an occlusion device in "free air". As is accepted in the art, the diameter of such an occlusion device is measured in free air. Accordingly, for the purposes of the present invention, and in one embodiment, the 14 resilient mesh body of the occlusion device is "oversized" relative to the 10 aneurysm and therefore has a diameter (x) greater than the diameter (y) of the 10 aneurysm (i.e., Φx>Φy) to be treated as shown in FIGS. 1A and 1B and in FIGS. 3A and 3B; i.e., diameter (y) is the greatest diameter of the 10 aneurysm to be treated or is one of the greater diameters of the 10 aneurysm so long as the 14 mesh body is oversized in such a manner so as to sufficiently seal the 22 neck of the 10 aneurysm to trigger clot formation and/or healing of the 10 aneurysm. An exemplary range of the diameter (x) of the occlusion device disclosed herein is approximately 6-30 millimeters (mm) and an exemplary diameter (y) of the aneurysm to be treated is less than the value of x. For example, the diameter (x) of the occlusion device is any of 7 mm, 11 mm, and/or 14 mm. In one embodiment, the position of the 34 distal end of the substantially solid 16 marker is attached approximately equidistantly from the opposing ends of the 14 resilient mesh body. Such a positioning of the 16 marker on the intrasaccular 14 resilient mesh body confers full retrievability of the occlusion device disclosed herein.

In another embodiment, the occlusion device disclosed herein is "oversized" relative to any vessel to be treated, such as, in pathological conditions in which vessel occlusion is desired, e.g., in peripheral vascular disease. In this instance, the diameter (x) of the occlusion device is greater than the diameter (z) of any vessel to be treated so long as the 14 body of the occlusion device is capable of conforming to vessel walls and promoting clot formation.

Figure 3B:
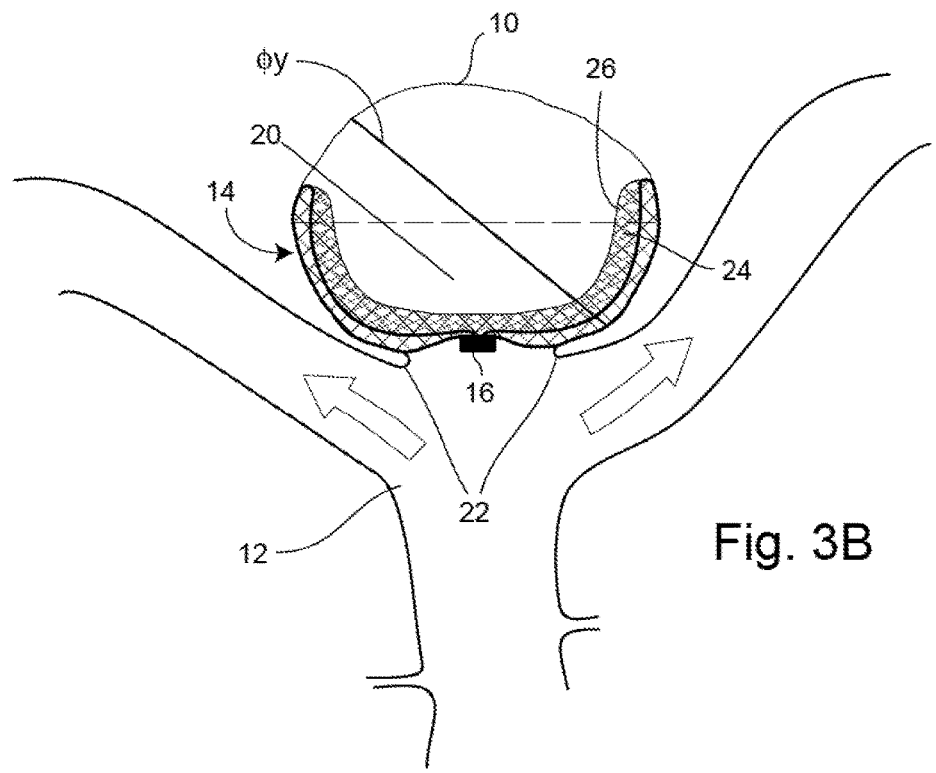

FIG. 1B and FIG. 3B show an embodiment of an occlusion device as disclosed herein deployed within an 10 aneurysm to be treated. FIG. 1B and FIG. 3B show the diameter (y) of such an 10 aneurysm to be treated and also shows the blood flow (arrows) in the 12 parent vessel (and basilar artery) adjacent to the 10 aneurysm and its 22 neck. In one embodiment, the 14 resilient mesh body of the occlusion device, when in free air and when deployed, is a "low profile" configuration.

For the purposes of the present invention, the terminology "low profile" means that the 14 resilient mesh body, in free air, has a 32 height that is between about 10-20% of its width, and therefore in its deployed shape the 14 resilient mesh body lays flush, in a flattened manner, up against the 10 aneurysm walls and is positioned to cover at least the interior surface of the 20 lower portion of the 10 aneurysm and seal the 22 neck of the 10 aneurysm. In this manner, the occlusion device disclosed herein is lower and/or slimmer than occlusion devices readily available in the art which expand to fill the space of the 10 aneurysm dome (fully and/or partially with respect to the majority of the space in the 10 aneurysm) and which expand radially and/or which expand in a spherical manner. In one embodiment, the 14 resilient mesh body, in free air, has a 32 height between about 12-18% of its width. In another embodiment, the 14 resilient mesh body, in free air, has a 32 height between about 14-16% of its width. In another embodiment, the 14 resilient mesh body, in free air, has a 32 height of about 15% of its width. In one embodiment, the deployed shape of the low profile 14 resilient mesh body covers between about 40%-80% of the inner surface area of the 10 aneurysm dome. In another embodiment, the deployed shape of the low profile 14 resilient mesh body covers between about 50%-70% of the inner surface area of the 10 aneurysm dome. In another embodiment, the deployed shape of the low profile 14 resilient mesh body covers about 60% of the inner surface area of the 10 aneurysm dome.

In another embodiment, the low profile, winged shaped and/or open-ended expanded spread configuration of the 14 body is a single layer of resilient mesh material. In another embodiment, the low profile, expanded spread configuration is a 24 dual (or double) layer of resilient mesh material. As described above, such a 14 resilient mesh body is "oversized" in comparison to the 10 aneurysm to be treated; and therefore the 14 mesh body has a diameter (x) greater than the diameter (y) of the 10 aneurysm to be treated (i.e., the greatest diameter or one of the greater diameters of the 10 aneurysm to be treated so long as the 14 mesh body is oversized in such a manner so as to sufficiently seal the 22 neck of the 10 aneurysm to trigger clot formation and/or healing of the 10 aneurysm). The low profile and oversizing attributes of the 14 resilient mesh body confer its capabilities for conforming to the inner surface of the walls of the 10 aneurysm (via the opposing pressure of the 14 body against the 10 aneurysm walls) and therefore the occlusion device expands in only at least the 20 lower portion (i.e., in a low volume flattened manner) of the 10 aneurysm along the 10 aneurysm walls, thereby eliminating the need for material to pin the 22 neck of the 10 aneurysm and/or to anchor within the 12 parent vessel (and thereby minimizing the need for anti-coagulation therapy). In this manner, the wing-span and/or expanded spread of the 14 body conforms to the interior surface of the 10 aneurysm and apposes the 10 aneurysm dome. Such a configuration facilitates sealing of the 22 neck of the 10 aneurysm and therefore clot formation and/or healing and/or shrinkage of the 10 aneurysm which is particularly advantageous if the size or mass of the 10 aneurysm is causing pain or other side effects within the patient. Such a configuration is also advantageous because it requires a minimum amount of resilient mesh material thereby eliminating the need to fill or substantially fill, in a spherical, radially expanded manner, the space in the 10 aneurysm dome. Such an occlusion device is well suited for conformability across a broad range of 10 aneurysm morphologies, particularly since it is well known and generally accepted that 10 aneurysms are not perfectly round in shape. It is also advantageous because an occlusion device as disclosed herein, having a "minimum of" or less material than the current standard devices, minimizes the need for anti-coagulation therapy and/or lessens the risk of clot emboli formation which could flow deeper into the vascular tree inducing stroke.

In another embodiment of an occlusion device disclosed herein, the single layer or 24 dual layer of resilient mesh material of the low profile device comprises a relatively uniform distribution of wire mesh strands or braids such as, without limitation, a 72 nitinol (NiTi) wire mesh strand braided configuration. In other embodiments, the occlusion device comprises wire mesh strands or braids that range from 36 to 144 NiTi strand braided configuration.

In another embodiment, as shown in FIGS. 3A-3B and FIGS. 4A-4C, a 24 dual layer occlusion device disclosed herein is a configuration of wire mesh which is folded circumferentially (26 circumferential fold line) and therefore doubled back on itself. The ends of the 24 dual or doubled back layer intersect with the 16 marker positioned approximately at the core of the 14 body of the device. In this regard, the device is constructed by circumferentially folding a single layer of mesh material over itself on a preferential 26 fold line effectively resulting in an occlusion device comprising a 24 dual layer of wire mesh material, i.e., the 24 dual layer of mesh comprises a single layer of mesh folded circumferentially (26 circumferential fold line). Without wishing to be bound by theory, this 24 doubled or dual layer of wire mesh material triggers a mechanism of action believed to contribute to the enhanced acute thrombogenicity of the device in animal studies. It is believed that the localizing of a small volume of clot between the 24 dual/double layers, which have a high surface area contribution from the wire strands, facilitates nucleating and stabilizing thrombus. In the deployed shape, the 14 body having a folded back 24 dual layer is deeper when compared to a non-deployed 24 dual layer occlusion device accounting for a change in width of approximately 15% which translates to an increase in the diameter (x) of the device when pressure is applied at the 16 marker. This change in width/increase in diameter (x) is an effective anchoring feature of the deployed device as blood applies pressure to the mesh 14 body distributed across the 22 neck of the 10 aneurysm. Such a configuration also provides sufficient apposition of the 14 body of the device against the 10 aneurysm wall or vessel wall for peripheral arterial or venous occlusion. Based on animal studies to date, it is clear the device disclosed herein provides sufficient mesh density to confer stasis acutely. It is further known, based on analyzing the device in post-deployment that the wire mesh/braid distribution remains relatively uniform.

Figure 4A:
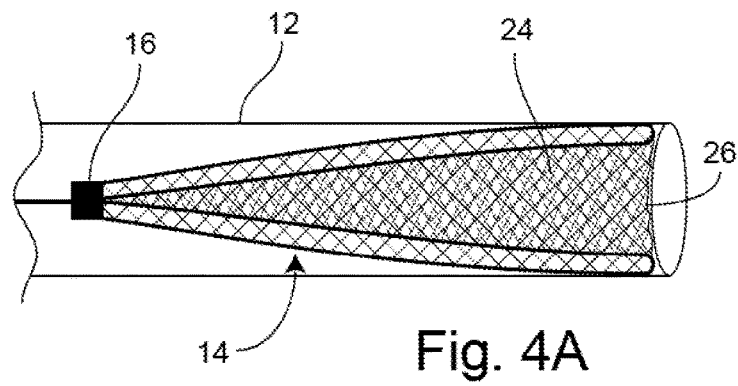
FIG. 4A-4C illustrates perspective views of an embodiment of the delivery and/or deployment of an occlusion device disclosed herein.
Figure 4B:
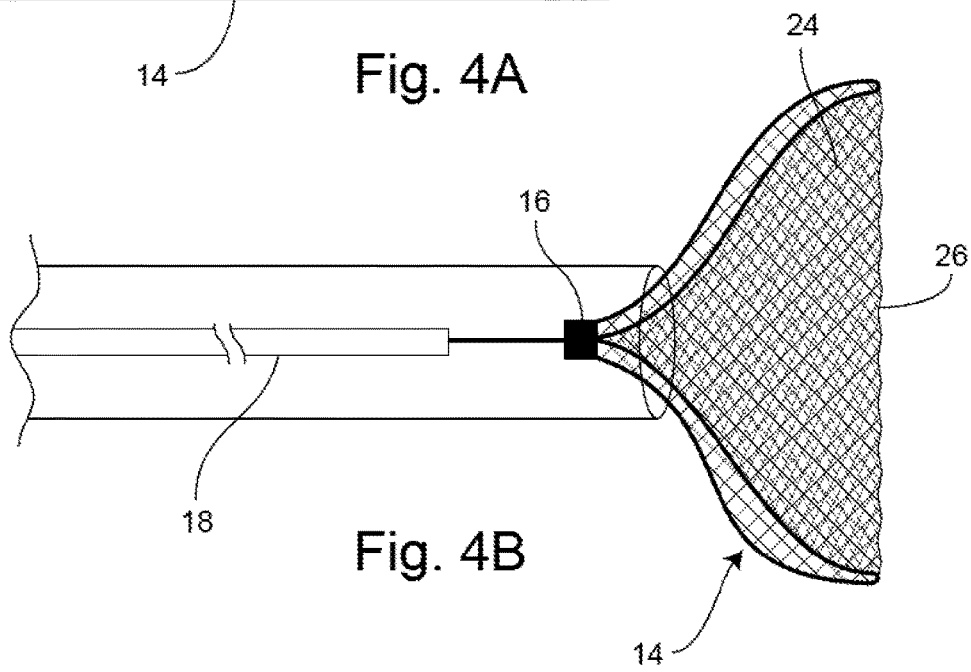
Figure 4C:
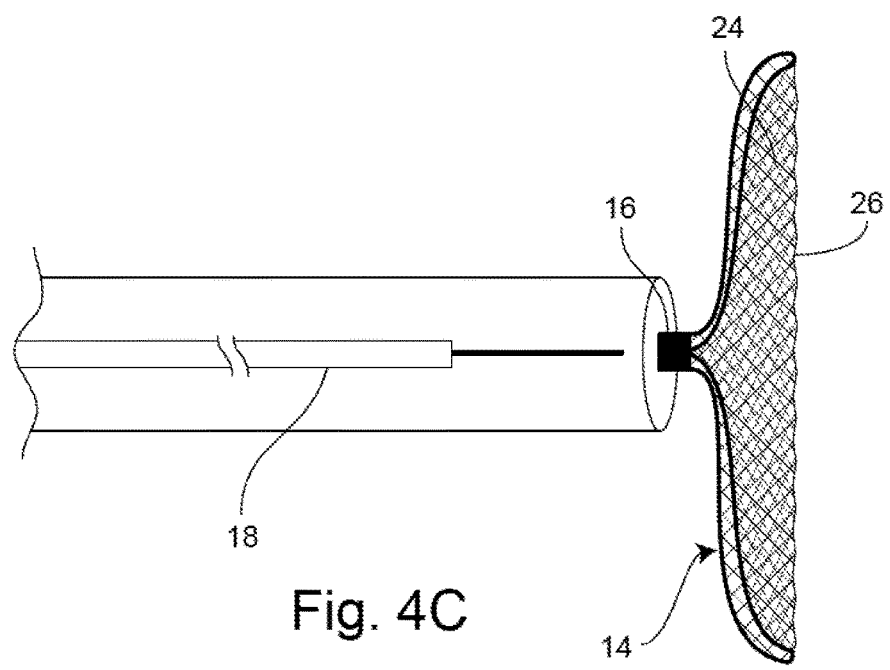

FIG. 1B and FIG. 4B also show the position of the 16 marker, having a 36 proximal end and a 34 distal end, on an occlusion device of the present invention. The 34 distal end of the 16 marker is attached to the 14 resilient mesh body of the occlusion device. The 36 proximal end of the 16 marker is shown resting across, in the manner of a bridge-like mechanism, the 22 neck of the 10 aneurysm to be treated, which when combined with the properties of the low profile 14 resilient mesh body, eliminates the need for incorporating additional material to pin the 22 neck of the 10 aneurysm and/or as an anchor within the 12 parent vessel and advantageously provides for full retrievability of the device.

In one embodiment, the 16 marker of the occlusion device disclosed herein is a substantially solid collar or rigid member such as, without limitation a solid ring comprised of materials such as, without limitation, gold, platinum, stainless steel, and/or combinations thereof. In another embodiment, radiopaque materials such as, without limitation, gold, platinum, platinum/iridium alloy, and/or combinations thereof, can be used. Such a 16 marker provides visualization of the device during delivery and placement. The 16 marker is positioned within the occlusion device so that the 36 proximal end of the 16 marker is capable of resting above the 22 neck of an 10 aneurysm. The solidness of the 16 marker helps confer stability of the device within the 10 aneurysm and prevents movement or the transfer of forces through the resilient mesh of the 14 body thereby preventing misplacement or accidental movement of the device. The 16 marker is also configured with a junction to cooperate and release from/attach to a corresponding delivery means such as, without limitation, a delivery catheter or guide wire and/or 18 pusher wire technologies. It also advantageously provides for full retrievability of the device disclosed herein.

In another embodiment, the substantially solid 16 marker comprises a radiopaque material (such as for example, without limitation, platinum, gold, platinum/iridium alloy, and/or combinations thereof) to facilitate visualization of the occlusion device under fluoroscopy during delivery, placement and/or deployment. The 16 marker comprises a 36 proximal end and a 34 distal end. A 14 resilient mesh body is attached to the 34 distal end and the 36 proximal end of the 16 marker may be configured to influence shape, diameter, and/or curvature of the 14 resilient mesh body upon expansion of the occlusion device. The 16 marker may be designed in various shapes to influence the overall profile of the occlusion device to ensure a proper fit of the expanded/deployed occlusion device within the 10 aneurysm sac.

Figure 2A:
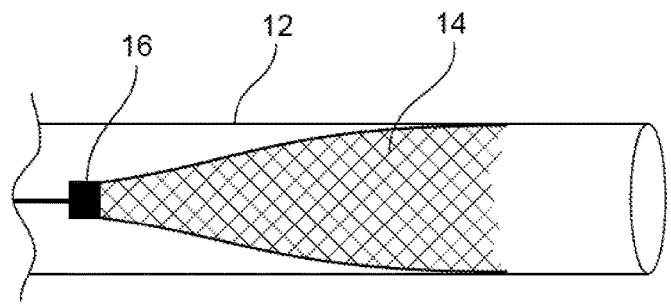
FIG. 2A-2C illustrates perspective views of an embodiment of the delivery and/or deployment of an occlusion device disclosed herein.
Figure 2B:
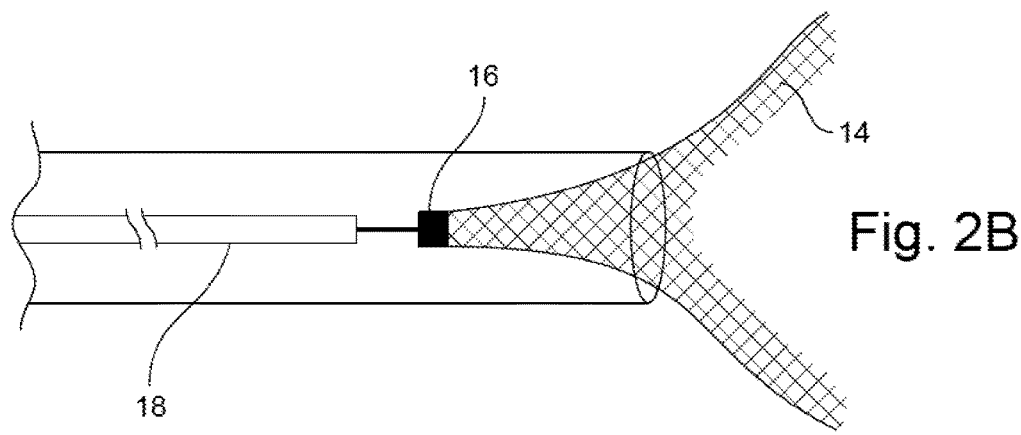
Figure 2C:
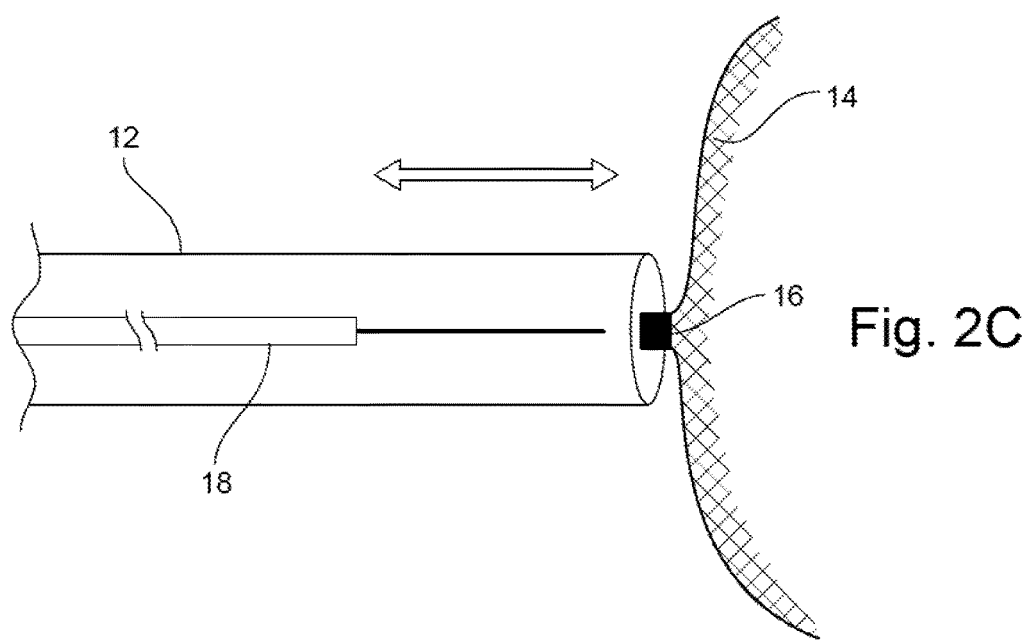

FIG. 2A-2C and FIG. 4A-C show an exemplary means for delivery and/or deployment, through an 12 artery and/or vessel adjacent to the 10 aneurysm, of the occlusion device disclosed herein. In one embodiment, the occlusion device is delivered in a closed, compacted position (delivery shape) as shown in FIGS. 2A and 4A, such that the low profile 14 body is closed inward on itself or compressed, via a 18 pusher wire mechanism. When the device is pushed into and/or placed in the 10 aneurysm sac, the ends of the low profile 14 resilient mesh body open outward in the manner of the opening of a flower (as shown in FIG. 2B and FIG. 4B) and the opened 14 body then conforms to the walls of the 10 aneurysm permitting the 16 marker to rest across the 22 neck and the low profile 14 body to lay flush in a flattened manner (deployed shape) covering at least the 20 lower portion of the 10 aneurysm and sealing the 22 neck of the 10 aneurysm. In one embodiment, as shown in FIG. 2C and in FIG. 4C, the device shows the deepening and/or flattening of the either the single layer (FIG. 2C) or 24 dual layer (FIG. 4C) device accounting for a change in width and an increase in the diameter (x) of the device when pressure is applied at the 16 marker. This change in width/increase in diameter (x) is an effective anchoring feature of the deployed device as blood applies pressure to the 14 body distributed across the 22 neck of the 10 aneurysm. Results of animal studies provided herein support that the circumferentially 24 doubled-over/dual-layer configuration provides efficient apposition of the mesh 14 body of the device against the 10 aneurysm wall or vessel for peripheral arterial or venous occlusion.

Figure 5A:
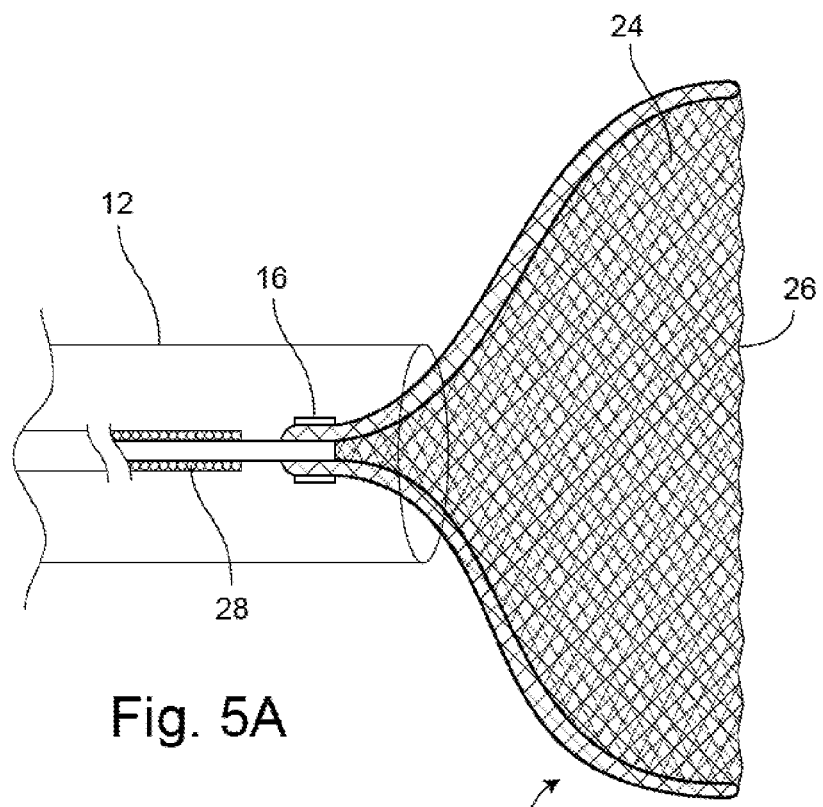
FIG. 5A-5B illustrates perspective views of an embodiment of the electrolytic delivery and/or deployment and/or detachment of an occlusion device disclosed herein.
Figure 5B:
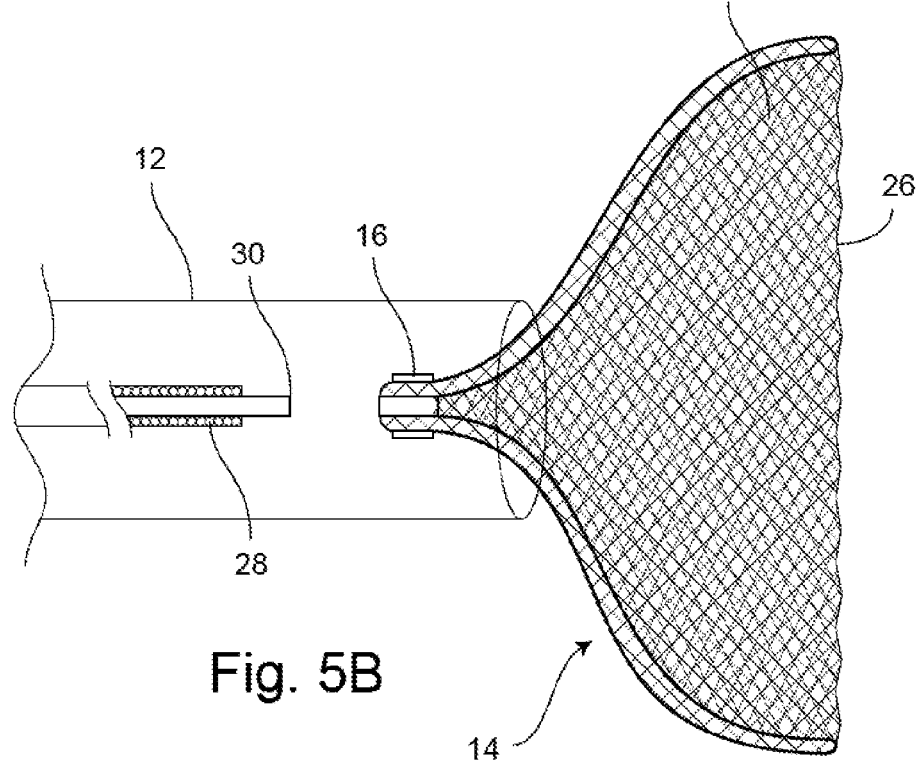

FIG. 5A-5B show an exemplary means for electrolytic delivery and/or deployment and/or detachment of the occlusion device disclosed herein through an 12 artery and/or vessel adjacent to the 10 aneurysm. Electrolytic detachment means and methods such as U.S. Pat. No. 5,122,136 are well known in the art. In one embodiment, a 28 coil-wound core wire (or guide wire) of the catheter (or micro-catheter) is attached inside the 16 marker at its 34 distal end to the 24 dual layer occlusion device disclosed herein (as shown in FIG. 5A). The coil wind maintains a constant diameter (Φ) so as not to impact upon flexibility or stiffness of the delivery catheter or micro-catheter or guide wire. In certain embodiments, FEP (Fluorinated Ethylene Propylene) heat shrink tubing encases the 28 coil-wound portion of the core wire. Numerous readily available and well known attachment techniques in the medical device arts can be used to attach the distal end of the core wire inside the 16 marker band and to the occlusion device or implant. Such attachment techniques include, without limitation, adhesives, laser melting, laser tack, spot, and/or continuous welding. In one embodiment, an adhesive is used to attach the distal end of the core wire inside the 16 marker band. In a further embodiment, the adhesive is an epoxy material which is cured or hardened through the application of heat or UV (ultra-violet) radiation. In an even further embodiment, the epoxy is a thermal cured, two-part epoxy such as EPO-TEK® 353ND-4 available from Epoxy Technology, Inc., 14 Fortune Drive, Billerica, Mass. Such an adhesive or epoxy material encapsulates the junction of the core wire inside the marker band and increases its mechanical stability.

In another embodiment, during and/or after deployment of the device, the 28 coil-wound core wire detaches the 24 dual layer occlusion device disclosed herein at an 30 electrolytic detachment site (or zone) on the core wire itself in such a manner so that the core wire is severed and/or dissolved through electrolytic action at the base of the 16 marker band (as shown in FIG. 5B). Such action then releases and/or places the 24 dual layer occlusion device into an aneurysm or vessel to be treated.

In certain embodiments, the low profile 14 resilient mesh body of the occlusion device disclosed herein can be filled with an embolic material to promote clotting and closure of the 10 aneurysm.

In other embodiments, the oversized occlusion device disclosed herein may further incorporate adjunctive elements and/or members such as coiling techniques, framing coils, embolic agents, additional markers, polymers, resorbent polymers and/or a combination thereof.

Resilient mesh materials for design and/or manufacture of occlusion devices are readily available and well known by those skilled in the relevant art. As such, resilient mesh materials range from a wide variety of available materials such as, without limitation, nickel titanium (nitinol or otherwise known as NiTi), stainless steel, polymers, and/or combinations thereof. Exemplary known biomedical polymeric families include, without limitation, polymers such as polyphosphazenes, polyanhydrides, polyacetals, poly(ortho esters), polyphosphoesters, polycaprolactones, polyurethanes, polylactides, polycarbonates, polyamides, and/or a combination thereof (See, e.g., J Polym Sci B Polym Phys. Author manuscript; available in PMC 2012 Jun. 15.)

In one exemplary embodiment, the resilient mesh material is formed of woven strands of polymer material, such as, without limitation, nylon, polypropylene or polyester. The polymer strands can be filled with a radiopaque material which allows the physician treating the aneurysm to fluoroscopically visualize the location of the device within the vasculature. Radiopaque filler materials preferably include bismuth trioxide, tungsten, titanium dioxide or barium sulfate, or radiopaque dyes such as iodine. The resilient mesh material can be formed by strands of radiopaque material. The radiopaque strands allow the physician and/or radiologist to fluoroscopically visualize the location of the mesh, without the use of filled polymer materials. Such radiopaque strands may be formed with materials such as, without limitation, gold, platinum, a platinum/iridium alloy, and/or a combination thereof. In one embodiment, the resilient mesh material is constructed of 10%-20% platinum core NiTi. In another embodiment, the resilient mesh material is constructed of 10% platinum core NiTi, 15% platinum core NiTi, or 20% platinum core NiTi. 10% platinum core NiTi construction is sufficient to provide a ghost image of the occlusion device under x-ray.

Such constructed combination wires or composite wires having a radiopaque core and non-radiopaque outer layer or casing are readily available and well known in the medical device and metallic arts as DFT® (drawn-filled-tube) wires, cables or ribbons. DFT® wire is a metal-to-metal composite constructed to combine the desired physical and mechanical attributes of two or more materials into a single wire. By placing the more radiopaque, but more ductile material in the core of the wire, the NiTi outer layer is able to provide the resulting composite wire with similar mechanical properties of a 100% NiTi wire. DFT® wires are available from Fort Wayne Metals Corp., Fort Wayne, Ind., U.S.A. See also, for example, the journal article entitled Biocompatible Wire by Schaffer in Advanced Materials & Processes, October 2002, pages 51-54, incorporated herein by reference.

Where the resilient mesh material is formed of radiopaque metal strands, the strands may be covered with a polymer coating or extrusion. The coating or extrusion over the radiopaque wire strands provides fluoroscopic visualization but also increases the resistance of the strands to bending fatigue and may also increase lubricity of the strands. The polymer coating or extrusion, in one embodiment, is coated or treated with an agent which tends to resist clotting, such as heparin. Such clot resistant coatings are generally known. The polymer coating or extrusion can be any suitable extrudable polymer, or any polymer that can be applied in a thin coating, such as Teflon® or polyurethane.

In yet another embodiment, the strands of the resilient mesh material are formed using both metal and polymer braided strands. Combining the metal strands with the polymer strands into a braid changes the flexibility characteristics of mesh. The force required to deploy and/or collapse such a mesh portion is significantly reduced over that required for a mesh portion that includes only metal mesh strands. However, the radiopaque characteristics of the mesh for fluoroscopic visualization are retained. Metal strands forming such a device includes, without limitation, stainless steel, gold, platinum, platinum/iridium, nitinol, and/or combinations thereof. Polymer strands forming the device can include nylon, polypropylene, polyester, Teflon®, and/or combinations thereof. Further, polymer strands of the mesh material can be chemically modified to make them radiopaque with known techniques such as, without limitation, by using gold deposition onto the polymer strands, or by using ion beam plasma deposition of suitable metal ions onto the polymer strands.

The resilient mesh material can also be formed with filaments or strands of varying diameter and/or varying flexibility. By varying the size or flexibility of the polymer strands, the flexibility characteristics of the mesh, upon deployment, can also be varied. By varying the flexibility characteristics, both the deployed and collapsed configuration of the 14 resilient mesh body can be varied or changed to substantially any desired shape.

Not only can the mesh be formed of both polymer strands or filaments and metal strands or filaments, but it can be formed using filaments of different polymer materials. For example, different polymer materials having different flexibility characteristics can be used in forming the mesh. This alters the flexibility characteristics to change the resultant configuration of the 14 mesh body in both the deployed and the collapsed positions. Such biomedical polymers are readily known and available in the art and can be derived from polymeric families such as, without limitation, polyphosphazenes, polyanhydrides, polyacetals, poly (ortho esters), polyphosphoesters, polycaprolactones, polyurethanes, polylactides, polycarbonates, polyamides, and/or a combination thereof.

Resilient mesh materials suitable for use within the 14 mesh body may take the form of a flat woven sheet, knitted sheet, or a laser cut wire mesh. In general, the material should include two or more sets of substantially parallel strands, with one set of parallel strands being at a pitch of between 45 degrees and 135 degrees with respect to the other set of parallel strands. In some embodiments, the two sets of parallel strands forming the mesh material are substantially perpendicular to each other. The pitch and general construction of the mesh material may be optimized to meet the performance needs of the occlusion device.

The wire strands of the metal fabric used in the present invention should be formed of a material which is both resilient and can be heat-treated to substantially set a desired shape. Materials which are believed to be suitable for this purpose include a cobalt-based low thermal expansion alloy referred to in the field of occlusion devices as Elgiloy®, nickel-based high-temperature high-strength "superalloys" commercially available from Haynes International under the trade name Hastelloy®, nickel-based heat treatable alloys sold under the name Incoloy® by International Nickel, and a number of different grades of stainless steel. The important factor in choosing a suitable material for the wires is that the wires retain a suitable amount of the deformation induced by the molding surface (or shape memory, as described below) when subjected to a predetermined heat treatment.

One class of materials which meet these qualifications are so-called shape memory alloys. Such alloys tend to have a temperature induced phase change which will cause the material to have a preferred configuration which can be fixed by heating the material above a certain transition temperature to induce a change in the phase of the material. When the alloy is cooled, the alloy will "remember" the shape it was in during the heat treatment and will tend to assume that same and/or similar configuration unless constrained from doing so.

One particular shape memory alloy for use in the present invention is nitinol, an approximately stoichiometric alloy of nickel and titanium, which may also include other minor amounts of other metals to achieve desired properties. NiTi alloys such as nitinol, including appropriate compositions and handling requirements, are well known in the art and such alloys need not be discussed in detail here. For example, U.S. Pat. Nos. 5,067,489 and 4,991,602, the teachings of which are incorporated herein by reference, discuss the use of shape memory NiTi alloys in guide wire-based technologies. Such NiTi alloys are preferred, at least in part, because they are commercially available and more is known about handling such alloys than other known shape memory alloys. NiTi alloys are also very elastic. Indeed, they are said to be known as "superelastic" or "pseudoelastic." This elasticity will help an occlusion device as disclosed herein return to prior expanded configuration for deployment thereof.

The wire strands can comprise a standard monofilament of the selected material, i.e., a standard wire stock may be used. In some embodiments, 72 wire strands and/or 72 strand braid configuration may be used. In other embodiments, the occlusion device comprises wire mesh strands or braids that range from 36 to 144 NiTi strand braided configurations. If so desired, though, the individual wire strands may be formed from "cables" made up of a plurality of individual wires. For example, cables formed of metal wires where several wires are helically wrapped about a central wire are commercially available and NiTi cables having an outer diameter of 0.003 inches or less can be purchased. One advantage of certain cables is that they tend to be "softer" than the monofilament wires having the same diameter and formed of same material. Additionally, the use of a cable can increase the effective surface area of the wire strand, which will tend to promote thrombosis.

An occlusion device disclosed herein is configured with low profile resilient mesh material of a mesh density sufficient for functioning in such a manner as an endothelial cell scaffold within a vessel or across the 22 neck of the 10 aneurysm and thereby reducing blood flow by about 60% to trigger clot formation and/or healing of the 10 aneurysm. For the purposes of the present invention, the terminology "mesh density" means the level of porosity or the ratio of metal to open area of the 14 mesh body. Mesh density relates to the number and size of the openings or pores of the mesh and by the extent that the pores are open or closed in situations where opening or pore openness varies between delivery and deployment. Generally, a high mesh density region of a resilient mesh material has approximately about 40% or more metal area and about 60% or less open area.

In some embodiments, the 14 resilient mesh body may be formed uniformly of the same material; however such material may have different knitted, stitched, braided, and/or cut construction.

In other embodiments, the implantable occlusion device disclosed herein can be used for the process of peripheral vascular embolization (a process well known in the art and known to involve the shutdown of blood flow distal to a specified vascular point), for example, in the treatment and/or amelioration of peripheral arterial or venous pathologies and/or any related pathologies requiring vessel occlusion for the treatment thereof.

The occlusion device of the present invention may incorporate reasonable design parameters, features, modifications, advantages, and variations that are readily apparent to those skilled in the art in the field of occlusion devices.

EXAMPLES

Study protocol and justification for animal use was reviewed and approved by the Institutional Animal Care and Use Committee (IACUC) at ISIS Services and the procedures carried out under veterinarian supervision.

The rabbit elastase aneurysm model is a well-accepted and art-recognized model for testing novel neurointerventional devices and has been the subject of a number of clinical publications regarding efficacy and similarity to human response. (See, e.g., Altes et al. Creation of Saccular Aneurysms in the Rabbit: A Model Suitable for Testing Endovascular Devices. AJR 2000; 174: 349-354.) It therefore is readily accepted by the regulatory agencies as an appropriate test model. The model's coagulation system is highly similar to that of humans. In addition, the model has advantageous anatomical aspects in that the diameters of the rabbits' extra-cranial carotid arteries are highly similar to the diameter of extra-cranial carotid arteries in humans. Moreover, elastase-induced aneurysms have been shown to behave in a histologically similar manner as human aneurysms.

Example I

Non-detachable occlusion device lot 30680, Detachable occlusion device lot 30676, Aneurysm size 4.5 millimeters (mm) (height)×2.5 width A 5-F (5-French) sheath placed in the femoral artery through which a 5F Cordis catheter, lumen 0.035", length 65 centimeters (cm) and a 0.035" Terumo guide-wire access was gained into the carotid artery.

The non-detachable occlusion device was positioned into the aneurysm with the marker at the neck of the aneurysm and contrast runs performed at timed intervals. Immediately after deployment of the device, it was observed to be in a good position in the aneurysm and there was some slowing of flow. At 5 minutes post deployment, there was some stasis observed in the aneurysm. At 10 minutes post deployment, further stagnation in the aneurysm was observed and the device was repositioned closer to the aneurysm neck. At 15 minutes post deployment, stagnation of flow in the aneurysm was observed. When the device was removed from the aneurysm and heparin was given, flow into the aneurysm returned to pre-deployment status.

The non-detachable occlusion device was then removed and a 7 mm diameter occlusion device advanced into a 0.027" lumen microcatheter (ExcelsiorXT27, Stryker) using a 0.014" guide wire (Synchro2, Stryker). Advancement of the device in the catheter was noted to be smooth with low friction. The occlusion device was advanced to the neck of the aneurysm and deployed. Timed angiographic runs were performed. Immediately post deployment, there was stasis of flow observed in the aneurysm. At 5 minutes post deployment, a filling defect in the aneurysm was observed. At 10 minutes post deployment, thrombus in the aneurysm was observed. At 20 minutes post deployment, the 5F catheter removed. On completion of the procedure the animal was euthanized in accordance with the Standard Operating Procedure (SOP).

Example II

Non-detachable occlusion device lot 30680, Detachable occlusion device lot 30676, Aneurysm size 10 mm height×4 mm wide×3 mm neck A similar procedure to Example I was performed with the placement of the non-detachable device into the aneurysm neck. In this example, a 4F system was used to introduce the device into the 5F sheath and a "step" on the internal hub of the catheter was noted to cause the device to catch. The device was placed and timed angiographic runs obtained as before. Immediately post deployment, some flow reduction was observed in the aneurysm. At 5 minutes post deployment, a filling defect was observed in the aneurysm sac. At 10 minutes post deployment, an increase in size of the filling defect was observed.

This device was removed, angiography demonstrated that flow had returned to pre-deployment status in the aneurysm, and an implantable (detached) device was deployed using the same method as previously. The implant required some force initially to transition into the microcatheter from the loading sheath (possibly due to poor sheath to hub lumen compatibility) but once inserted, the microcatheter advanced freely.

The device was noted to have reasonable deployment control despite not being fixed to a detachment mechanism. Positioning was achieved to cover the neck of the aneurysm and timed angiographic runs obtained. Immediately post deployment, thrombosis was observed at a distal portion of the aneurysm. At 5 minutes post deployment, virtual occlusion of the aneurysm sac was observed. At 10 minutes post deployment, complete occlusion of the aneurysm sac was observed. At 15 minutes post deployment, occlusion of the aneurysm distal to the device marker was observed.

Activated Clotting Time (ACT) noted to be 2 times normal at the 5 minute post deployment angiogram. Blood pressure of the animal throughout the process had been at normal (85/55, mean 60-65 mm hg). Positioning of the device in the animal allowed stasis without compromising the underlying carotid and so the live animal will be re-evaluated at 30 days post study.

Example III

Detachable device lot 30676, Aneurysm size 6.5 mm×3.1 mm width×2.4 mm neck

The procedure followed the same protocol as Example II, however, on contrast agent injection it was noticed that the aorta had dissected. It was possible to deploy a device into the aneurysm neck and timed angiographic runs obtained as before.

Observations

This series of angiograms confirm the wire mesh braid configuration of the occlusion device disclosed herein is sufficiently dense to reduce blood flow in the aneurysm leading to stasis of blood and thrombosis in the aneurysm sac. The study, accounting for variability in animal morphology, allowed for the understanding and consideration of device development and its deployment technique.

All femoral punctures were carried out via femoral cut-downs with the use of a vein picker. The sheaths used were 5-F and specifically had very narrow tips allowing expansion of the femoral vessel without damaging it. The length of the catheter was an issue especially in the devices that were fixed on a wire. Hence, in all cases a foreshortened/hand cut catheter was used. This meant that the distal catheter tip was rather sharp and abrupt leading to problems like vessel dissections as in Example III. Despite this, which can be addressed by use of a microsheath, deployment (through the large guide catheter) of the occlusion device was smooth and corresponds to use of the device with a detachment mechanism.

Manipulation and deployment control of the occlusion device were carried out while visualizing the proximal radiopaque marker of the device in relation to the catheter tip. Device development will entail the incorporation of radiopaque struts of platinum core NiTi wire to aid in visibility.

The occlusion device in the animal studies was of limited expansion (7 mm). Device development will incorporate increased diameters of greater than 7 mm. Accordingly, such devices have been designed with diameters of 11 mm and 14 mm. Even so, despite limitations with expansion spread of the 7 mm devices, all deployments promoted stasis in the aneurysms and all devices were easy to manipulate with pinpoint accuracy, particularly in relation to guidance through the parent arteries and neck of the aneurysms and placement within the aneurysms across the neck of the aneurysms.

A number of embodiments of the invention have been described. Without departing from the scope and spirit of the present invention, reasonable features, modifications, advantages, and design variations of the claimed apparatus will become readily apparent to those skilled in the art by following the guidelines set forth in the preceding detailed description and embodiments. Accordingly, other embodiments are within the scope of the following claims.

What is claimed is:

1. A kit for treatment and/or amelioration of an aneurysm; the kit comprising
    a. an occlusion device for intrasaccular implantation consisting of (i) a substantially solid marker having a proximal end, and a distal end; and (ii) a resilient mesh body attached to the distal end of the marker, the body having a delivery shape and a deployed shape capable of conforming to aneurysm walls; wherein the body is a dual layer of the resilient mesh folded over onto itself to create a circumferential fold line around the circumference of the body, and folded over ends of the resilient mesh, and wherein all of the folded over ends of the dual layer of mesh are within the marker; and
    b. a delivery system or detachment system corresponding to the occlusion device.

2. The kit of claim 1, wherein the delivery system is a micro catheter, catheter, guide wire, or pusher wire.

3. The kit of claim 1, wherein the detachment system is an electrolytic detachment system.

4. An implantable device for vessel occlusion consisting of: (a) a substantially solid marker having a proximal end, and a distal end; and (b) a resilient mesh body attached to the distal end of the marker, the body having a delivery shape and a deployed shape capable of conforming to vessel walls; wherein the body is a dual layer of the resilient mesh folded over onto itself to create a circumferential fold line around the circumference of the body, and folded over ends of the resilient mesh, and wherein all of the folded over ends of the dual layer of mesh are within the marker.

5. The occlusion device of claim 4, wherein the deployed shape of the body is capable of apposing an aneurysm dome.

6. The occlusion device of claim 4, wherein the proximal end of the marker is capable of sealing an aneurysm neck.

7. The occlusion device of claim 4, wherein the marker is a radiopaque marker.

8. The occlusion device of claim 4, wherein the marker is a detachment junction to deploy the occlusion device.

9. The occlusion device of claim 4, wherein the marker is an attachment junction to retrieve the occlusion device.

10. The occlusion device of claim 4, wherein the marker comprises a rigid member.

11. The occlusion device of claim 4, wherein the marker is a solid ring.

12. The implantable device of claim 4, wherein the body is configured to have a diameter greater than a diameter of an aneurysm or vessel to be treated; and wherein the body has a height that is between about 10-20% of its width.

13. The occlusion device of claim 12, wherein the body has a height that is between about 12-18% of its width.

14. The occlusion device of claim 12, wherein the body has a height that is between about 14-16% of its width.

15. The occlusion device of claim 12, wherein the body has a height that is about 15% of its width.

* * * * *

US010130372C1

(12) EX PARTE REEXAMINATION CERTIFICATE (13067th)
United States Patent
Griffin

(10) Number: US 10,130,372 C1
(45) Certificate Issued: Oct. 27, 2025

(54) OCCLUSION DEVICE

(71) Applicant: Cerus Endovascular Limited, Oxford (GB)

(72) Inventor: Stephen Griffin, San Jose, CA (US)

(73) Assignee: STRYKER IRELAND TECHNOLOGY LTD., Carrigtwohill (IE)

Reexamination Request:
No. 90/019,490, Apr. 18, 2024

Reexamination Certificate for:
Patent No.: 10,130,372
Issued: Nov. 20, 2018
Appl. No.: 14/699,188
Filed: Apr. 29, 2015

Related U.S. Application Data

(60) Provisional application No. 62/083,672, filed on Nov. 24, 2014, provisional application No. 61/986,369, filed on Apr. 30, 2014.

(51) Int. Cl.
*A61M 29/00* (2006.01)
*A61B 17/12* (2006.01)
*A61B 90/00* (2016.01)
*A61B 17/00* (2006.01)

(52) U.S. Cl.
CPC ........ *A61B 17/12172* (2013.01); *A61B 17/12* (2013.01); *A61B 17/12031* (2013.01); *A61B 17/12113* (2013.01); *A61B 17/12168* (2013.01); *A61B 90/39* (2016.02); *A61B 2017/00867* (2013.01); *A61B 2017/1205* (2013.01); *A61B 2017/12063* (2013.01); *A61B 2090/3937* (2016.02)

(58) Field of Classification Search
None
See application file for complete search history.

(56) References Cited

To view the complete listing of prior art documents cited during the proceeding for Reexamination Control Number 90/019,490, please refer to the USPTO's Patent Electronic System.

*Primary Examiner* — Catherine S Williams

(57) ABSTRACT

Provided herein is an occlusion device for intrasaccular implantation and/or vascular occlusion comprising: (a) a substantially solid marker having a proximal end, and a distal end; and (b) a low profile resilient mesh body attached to the distal end of the marker, the body having a delivery shape and a deployed shape capable of conforming to aneurysm walls; wherein the body has a diameter greater than a diameter of an aneurysm to be treated. Also provided herein is a kit comprising the occlusion device disclosed herein and a means for delivery thereof. Methods of manufacture and use of the occlusion device disclosed herein are also disclosed.

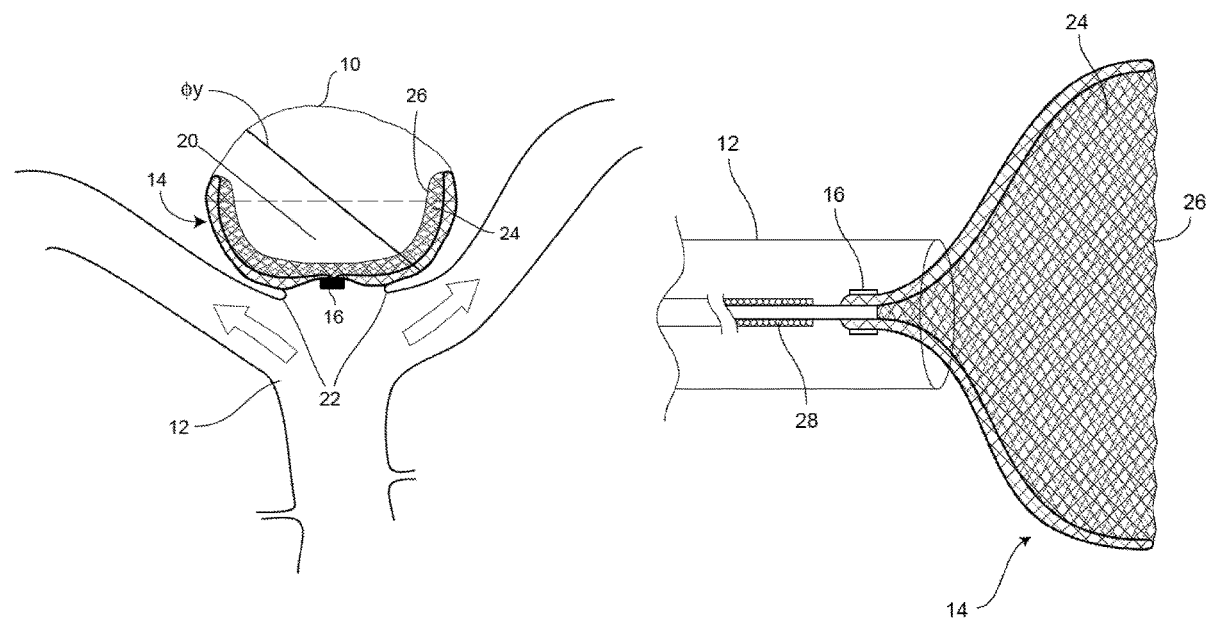

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 10-11 are cancelled.

Claims 1 and 4 are determined to be patentable as amended.

Claims 2-3, 5-9 and 12-15, dependent on an amended claim, are determined to be patentable.

New claim 16 is added and determined to be patentable.

1. A kit for treatment and/or amelioration of an aneurysm; the kit [comprising] *consisting essentially of:*
    a. an occlusion device for intrasaccular implantation [consisting] *without a need for an anchor within a parent vessel and without a need for additional material to pin the occlusion device at the neck, wherein the occlusion device consists* of:
       (i) a substantially solid marker having a proximal end, and a distal end; and
       (ii) a resilient mesh body attached to the distal end of the marker, the body having a delivery shape and a deployed shape capable of conforming to aneurysm walls; wherein the body is a dual layer of the resilient mesh folded over onto itself to create a circumferential fold line around the circumference of the body, and folded over ends of the resilient mesh, and wherein all of the folded over ends of the dual layer of mesh are within the marker*wherein, in free air, a height of the resilient mesh body is between about 10 percent to 20 percent of a width of the resilient mesh body*; and
    b. a delivery system or detachment system corresponding to the occlusion device.

4. An implantable device for vessel occlusion consisting of:
    (a) a substantially solid marker having a proximal end, and a distal end, *wherein the marker consists of a rigid member, wherein the proximal end of the substantially solid marker defines a proximal-most end of the implantable device for vessel occlusion*; and
    (b) a resilient mesh body attached to the distal end of the marker, the body having a delivery shape and a deployed shape capable of conforming to vessel walls;
    wherein the body is a dual layer of the resilient mesh folded over onto itself to create a circumferential fold line around the circumference of the body, and folded over ends of the resilient mesh, and wherein all of the folded over ends of the dual layer of mesh are within the marker.

*16. The occlusion device of claim 4, wherein the marker is a solid ring.*

\* \* \* \* \*